(12) United States Patent
Namm

(10) Patent No.: US 10,603,527 B2
(45) Date of Patent: Mar. 31, 2020

(54) BODY-WEARABLE GARMENT HAVING A HOOD ACTIVATED SPEAKER

(71) Applicant: MOTOROLA SOLUTIONS, INC., Chicago, IL (US)

(72) Inventor: Joseph C. Namm, Plantation, FL (US)

(73) Assignee: MOTOROLA SOLUTIONS, INC., Chicago, IL (US)

( * ) Notice: Subject to any disclaimer, the term of this patent is extended or adjusted under 35 U.S.C. 154(b) by 302 days.

(21) Appl. No.: 15/697,844

(22) Filed: Sep. 7, 2017

(65) Prior Publication Data

US 2019/0070439 A1 Mar. 7, 2019

(51) Int. Cl.
| | |
|---|---|
| *A62B 17/04* | (2006.01) |
| *H04R 1/02* | (2006.01) |
| *A61B 5/01* | (2006.01) |
| *A61B 5/00* | (2006.01) |
| *A62B 9/00* | (2006.01) |
| *H04R 3/00* | (2006.01) |
| *A41D 1/00* | (2018.01) |
| *A61B 5/0476* | (2006.01) |
| *H04R 1/10* | (2006.01) |

(52) U.S. Cl.
CPC .............. *A62B 17/04* (2013.01); *A41D 1/005* (2013.01); *A61B 5/01* (2013.01); *A61B 5/6803* (2013.01); *A61B 5/6844* (2013.01); *A61B 5/7405* (2013.01); *A62B 9/006* (2013.01); *H04R 1/028* (2013.01); *H04R 3/00* (2013.01); *A41D 2200/20* (2013.01); *A41D 2600/20* (2013.01); *A61B 5/0476* (2013.01); *A61B 2503/20* (2013.01); *A61B 2560/029* (2013.01); *A61B 2560/0252* (2013.01); *A61B 2562/0257* (2013.01); *H04R 1/1041* (2013.01); *H04R 2201/023* (2013.01); *H04R 2420/07* (2013.01); *H04R 2460/03* (2013.01)

(58) Field of Classification Search
CPC ....... A61B 5/01; A61B 5/6803; A61B 5/6844; A61B 5/7405; A61B 2562/0257; A62B 17/04; A41D 1/005; A41D 2200/20; H04R 2201/023; H04R 2420/07
See application file for complete search history.

(56) References Cited

U.S. PATENT DOCUMENTS

| | | | | |
|---|---|---|---|---|
| 6,707,922 B2* | 3/2004 | Tilbury | ..................... | H04R 5/02 181/153 |
| 6,748,025 B1* | 6/2004 | Hickling | .............. | H04B 1/0014 341/143 |
| 7,864,755 B2* | 1/2011 | Takahashi | ............... | H04W 8/08 370/238 |
| 9,322,121 B2* | 4/2016 | Dunne | ................... | D05B 97/12 |
| 2008/0276933 A1* | 11/2008 | Dampney | ................ | A42B 3/28 128/201.25 |
| 2009/0235426 A1* | 9/2009 | Johnston | ................ | A41D 3/005 2/84 |
| 2015/0370320 A1 | 12/2015 | Connor | | |
| 2016/0331320 A1 | 11/2016 | Durbhaka et al. | | |

* cited by examiner

*Primary Examiner* — Brian Ensey
(74) *Attorney, Agent, or Firm* — Perry + Currier, Inc.

(57) ABSTRACT

A body-wearable garment having a hood activated speaker is provided. The body-wearable garment comprises a hood. The body-wearable garment further comprises a speaker integrated within the hood. The speaker is activated in response to receiving a signal from a sensor indicating that the hood is in a deployed state.

19 Claims, 8 Drawing Sheets

STORED STATE

BODY-WEARABLE GARMENT HAVING A HOOD ACTIVATED SPEAKER

BACKGROUND OF THE INVENTION

Prior to entering an "immediately dangerous to life and health" (IDLH) environment, a firefighter will put on personal protective equipment which may include a fire-retardant hood, often used with a self-contained breathing apparatus (SCBA) mask. However, the firefighter still needs to maintain radio contact with other firefighters, a dispatch, and the like when the IDLH environment is entered.

BRIEF DESCRIPTION OF THE SEVERAL VIEWS OF THE DRAWINGS

The accompanying figures, where like reference numerals refer to identical or functionally similar elements throughout the separate views, together with the detailed description below, are incorporated in and form part of the specification, and serve to further illustrate embodiments of concepts that include the claimed invention, and explain various principles and advantages of those embodiments.

Figure 1:
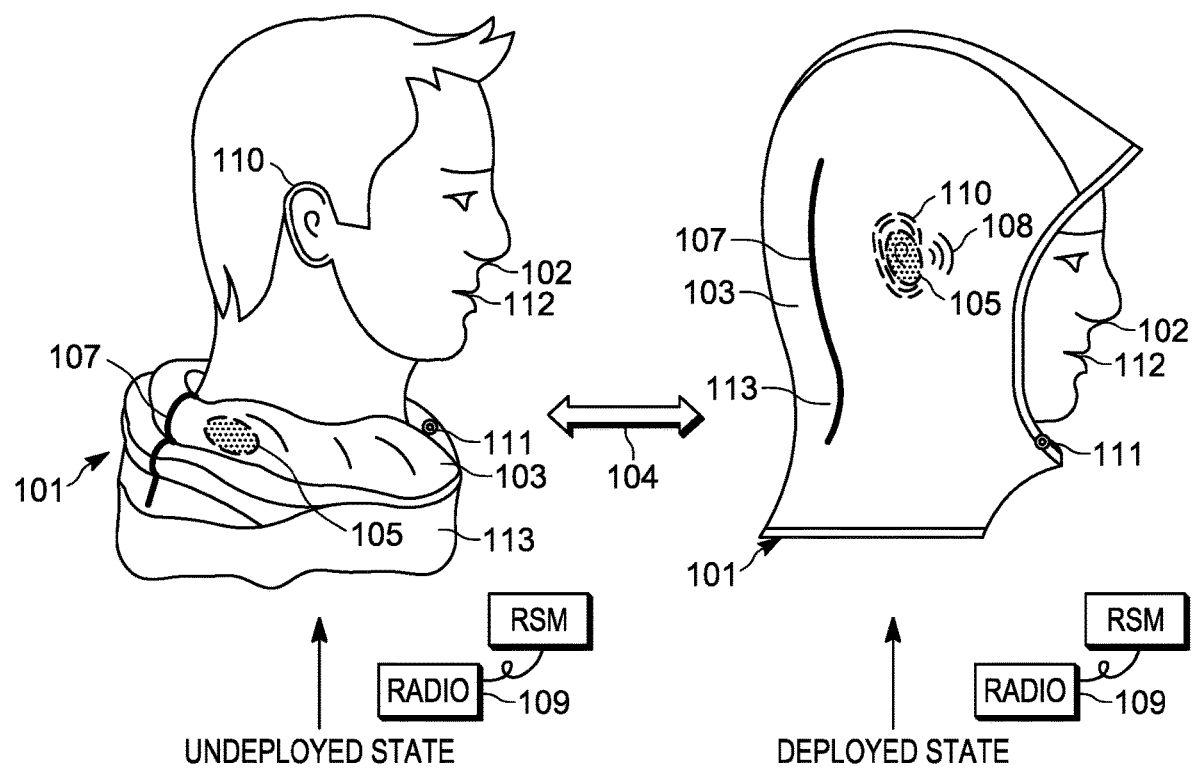
FIG. 1 is a schematic diagram of a body-wearable garment that includes a speaker in a hood, and an optional microphone, each of which is activated when the hood is in a deployed state and deactivated when the hood in undeployed state, in accordance with some embodiments.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

The apparatus and method components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

DETAILED DESCRIPTION OF THE INVENTION

When a firefighter, and the like, enters an "immediately dangerous to life and health" (IDLH) environment, they will put on a personal protective equipment which may include a fire-retardant hood, often used with a self-contained breathing apparatus (SCBA) mask. However, the firefighter still needs to maintain radio contact with other firefighters, a dispatch, and the like when the hood is deployed and the IDLH environment is entered. Use of a remote speaker-microphone (RSM) of a radio may be awkward and/or difficult in such situations. Furthermore, there is often urgency when entering the IDLH environment, and setting up specialized radio equipment may lead to delays.

Hence, the present specification provides a body wearable garment, comprising: a hood; and a speaker integrated within the hood, the speaker being activated in response to receiving a signal from a sensor indicating that the hood is in a deployed state.

Attention is directed to a FIG. 1 which depicts a body-wearable garment 101 (interchangeably referred to hereafter as the garment 101) being worn by a wearer 102. The garment 101 generally comprises a hood 103 which is depicted in an undeployed state (e.g. on the left-hand side of FIG. 1), in which the hood 103 is gathered at a neck of the wearer 102, and further depicted in a deployed state (e.g. on the right-hand side of FIG. 1), in which the hood 103 is lifted around a head of the wearer 102. The hood 103 may be moved between the undeployed state and the deployed state by the wearer 102, as represented by the double arrow 104, for example by the wearer 102 lifting the hood 103 from the undeployed state to the deployed state, and/or by the wearer 102 lowering the hood 103 from the deployed state to the undeployed state.

The garment 101 further comprises a speaker 105 integrated within the hood 103, the speaker 105 being activated in response to receiving a signal from a sensor 107 indicating that the hood 103 is in a deployed state. Indeed, as depicted in the deployed state, the speaker 105 is emitting sound 108, but not emitting sound in the undeployed state. For example, the speaker 105 may be receiving sound signals and/or sound data from a radio 109, and the like. As depicted, the radio 109 includes a remote speaker-microphone RSM which may be used by the wearer 102 for audio communications with the radio 109.

However, while present embodiments are described with respect to the speaker 105 receiving sound signals, and the like, from the radio 109, in other embodiments, the speaker 105 may be receiving sound signals, and the like, from other types of audio devices including, but not limited to, a cell phone, an MP3 player, and the like.

In FIG. 1, an exterior surface of the hood 103 is depicted, and the speaker 105 is depicted in broken lines indicating that the speaker 105 is located at an interior surface of the hood 103.

Furthermore, the speaker 105 is generally located at the interior surface such that, when the hood 103 is in the deployed state, the speaker 105 is located adjacent an ear 110 of the wearer 102. Hence, in the undeployed state, the ear 110 of the wearer 102 is uncovered by the hood 103, and in the deployed state, the ear 110 of the wearer 102 is covered by the hood 103 with the speaker 105 located adjacent the ear 110. As such, in FIG. 1, in the deployed state, the ear 110 of the wearer 102 is also depicted in broken lines.

As depicted, the garment 101 further comprises an optional microphone 111, the optional microphone 111 also being activated in response to receiving the signal from the sensor 107 indicating that the hood 103 is in the deployed state. The microphone 111 may be located at the interior surface or exterior surface of the hood 103, and/or at a location of the garment 101 not on the hood 103, the location selected such that, when the hood 103 is in the deployed sate, the microphone 111 is located to receive sound from a mouth 112 of the wearer 102, which may, in turn, be transmitted to the radio 109.

Hence, together the speaker 105 and the microphone 111 comprise an audio system (e.g. for use with the radio 109) that may be rapidly activated by deploying the hood 103, and rapidly deactivated by un-deploying the hood 103.

In some embodiments, the hood 103 may be adapted for use by a firefighter, and the like. Hence, while not depicted in FIG. 1, the hood 103 may be adapted for use with a mask including, but not limited to, a self-contained breathing apparatus (SCBA) mask (e.g. see FIG. 12). Furthermore, the garment 101 and/or the hood 103 may comprise a fire-retardant material, including, but not limited to, Nomex™ and the like, such that the garment 101 is generally configured for use by firefighters. Indeed, as depicted, the garment 101 further includes a neck portion 113 extending from a bottom portion of the hood 103 (e.g. relative to the wearer 102 when the garment 101 is worn) which may provide further protection and/or extend over a firefighting uniform and the like.

However, the hood 103 may comprise a fabric, and the like, which is not fire-retardant such that the garment 101 may be generally configured for use by first-responders who are not fire-fighters, for example police officers, under-cover police officers). Indeed, as the speaker 105 is generally located at an interior surface of the hood 103, the speaker 105 may not be visible when the garment 101 is worn by the wearer 102, whether in the deployed state or undeployed state; similarly, the microphone 111, when present, maybe located at the interior surface of the hood 103 and/or camouflaged such that the microphone 111 may not be visible when the garment 101 is worn by the wearer 102, whether in the deployed state or undeployed state. Hence, the audio system represented by the speaker 105 and the microphone 111 may be used in undercover police officer scenarios.

However, the garment 101 may optionally be used by the general public and/or any user who wishes to use the garment 101 for audio communication. For example, the garment 101 may comprise a "hoodie" (e.g. a sweater-type garment having a hood), and the like, that includes sleeves, pockets and the like.

The speaker 105 may comprise any speaker that may be integrated with the hood 103 including, but not limited to, a flexible speaker. However, when the garment 101 is to be used by firefighters and/or first responders, the speaker 105 is generally configured for use in firefighting and/or first responder environments; as such, the speaker 105 may be tolerant to high temperatures and/or may, when activated, be operated in a whisper mode such that the sound 108 may be heard by the wearer 102, but otherwise is low enough to not be heard by others near the wearer 102. For example, the sound 108 may be lower than a threshold sound level which may be configurable.

Similarly, the microphone 111 may comprise any microphone that may be integrated with the hood 103 including, but not limited to, a flexible microphone. However, when the garment 101 is to be used by firefighters and/or first responders, the microphone 111 is generally configured for use in firefighting and/or first responder environments; as such, the microphone 111 may be tolerant to high temperatures.

The sensor 107 is generally configured to sense whether the hood 103 is in the undeployed state or the deployed state. For example, the sensor 107 may be configured to: sense the hood 103 being in an undeployed state when the hood 103 is folded; and sense the hood 103 being in the deployed state when the hood 103 is unfolded.

As depicted in FIG. 1, the sensor 107 may comprise conductive thread in the hood 103, which changes conductivity depending on whether the conductive thread is folded and/or bent, or not folded and/or not bent. For example, the conductivity of the conductive thread may be higher when bent than when not bent. While the conductive thread is depicted in FIG. 1 as being at an external surface of the hood 103 (and/or the garment 101), the conductive thread may be woven into a fabric of the hood 103 (and/or the garment 101) and/or located at an external surface.

Hence, as depicted in FIG. 1, the conductive thread of the sensor 107 arranged in a direction along the hood 103 such that: when the hood 103 is undeployed, the conductive thread is folded and/or bent; and when the hood 103 is deployed, the conductive thread is not folded and/or not bent (and/or has fewer folds and/or bends than in the undeployed state).

Figure 3:
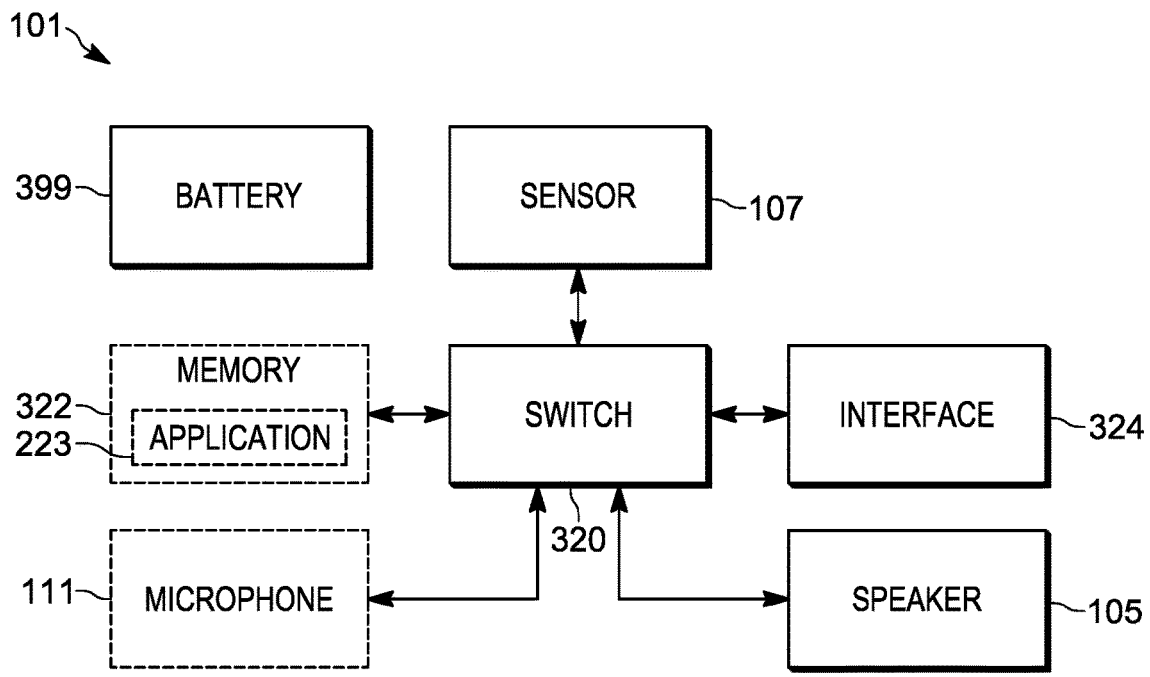
FIG. 3 is a block diagram of electrical components of the body-wearable garment of FIG. 1 in accordance with some embodiments.

The sensor 107 may hence further include a detector for detecting a conductivity of the conductive thread, including, but not limited to, a conductivity meter and/or a resistance meter and/or a Wheatstone bridge, using, for example, current provided by a battery and/or power source of the garment 101 (e.g. see FIG. 3). When the measured conductivity of the conductive thread is below a threshold value, the sensor 107 produces a signal indicating that the hood 103 is in a deployed state; and when the when the measured conductivity of the conductive thread is below the threshold value, the sensor 107 produces a signal indicating that the hood 103 is in an undeployed state. The threshold value may be configured based on the changes in conductivity of the conductive thread in the different physical states (e.g. bent/not-bent, and the like).

Figure 8:
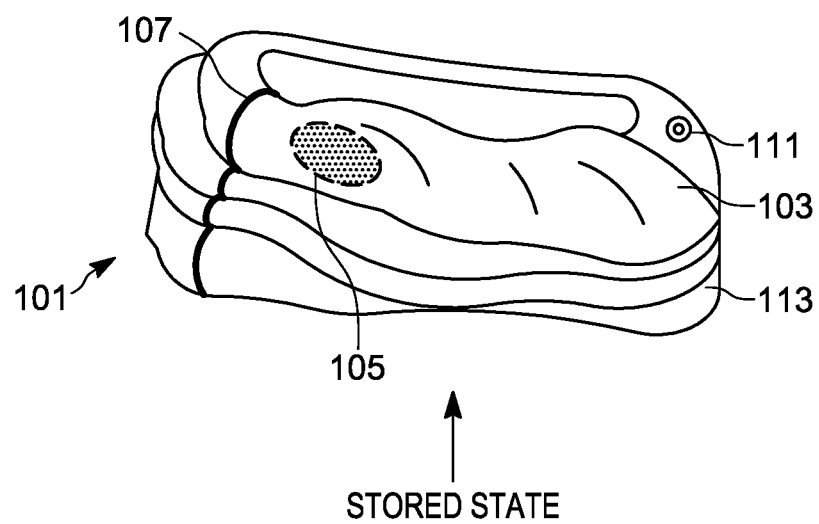
FIG. 8 is a schematic diagram of the body-wearable garment in a stored state in accordance with some alternative embodiments.

As further depicted in FIG. 1, the sensor 107 in the form of the conductive thread extends into the neck portion 113; hence, in the depicted embodiments, the sensor 107 may be further configured to detect when both the hood 103 and the neck portion 113 are both folded and/or bent, or not folded and/or not bent, as the conductivity of the conductive thread will be higher than when the hood 103 is deployed (e.g. not folded), and when only the hood 103 is undeployed (e.g. folded), as more bends in the conductive thread will be present (e.g. as depicted in FIG. 8). Both the hood 103 and the neck portion 113 being folded may indicate that the garment 101 and/or the hood 103 is in a stored state (e.g. e.g. the garment 101 is folded and stored, for example in a storage locker and/or a storage facility).

Figure 2:
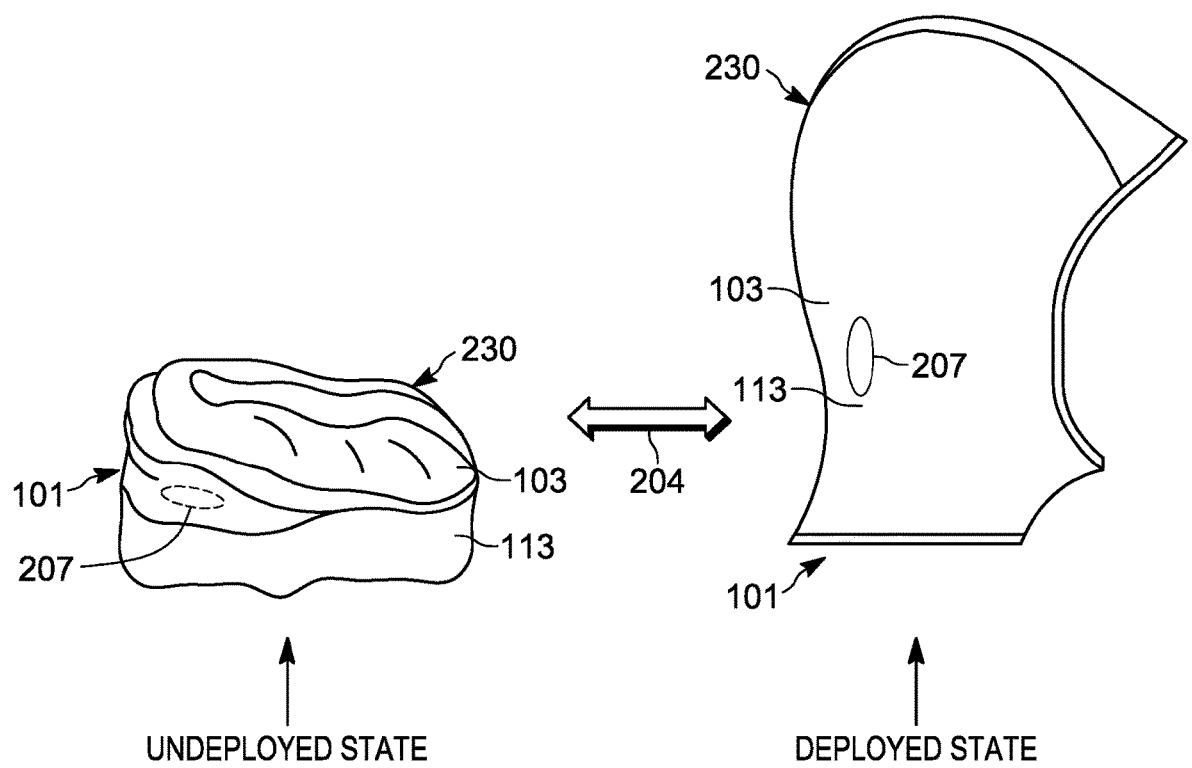
FIG. 2 is a schematic diagram of a body-wearable garment, in an undeployed state and a deployed state, the body-wearable garment including one or more proximity sensors in accordance with some alternative embodiments.

Alternatively, the sensor 107 may comprise one or more proximity detectors at the hood 103 located to detect when the hood 103 is folded and unfolded. For example, attention is directed to FIG. 2 which depicts a schematic of an alternative embodiment of the hood 103 of the garment 101 being changed between the undeployed state and the deployed state (as indicated by the double-arrow 204). In the embodiment of FIG. 2, the sensor 107 of FIG. 1 has been replaced with a proximity detector 207 located on an external surface 230 of the hood 103. The proximity detector 207 is located at a position where: in the undeployed (e.g. folded) state, the proximity detector 207 is located in a fold of the external surface 230 such that the proximity detector 207 detects another portion of the external surface 230; and in the deployed (e.g. unfolded) state, the proximity detector 207 is not located in a fold of the external surface 230 such that the proximity detector 207 does detect another portion of the external surface 230. Hence, when the hood 103 is in the undeployed state, the proximity detector 207 generates a signal, and the like, indicating a proximity detection and, when the hood 103 is in the deployed state, the proximity detector 207 generates a signal, and the like, indicating no proximity detection.

In yet further implementations, one or more similar proximity sensors may be located at the neck portion 113 to detect when the neck portion 113 is folded or not folded, which may indicate that the garment 101 and/or the hood 103 is in a stored state.

Furthermore, one or more proximity detectors, similar to the proximity detector 207 of FIG. 2, may be used in combination with conductive thread of the sensor 107 of FIG. 1 such that a sensor of the garment 101 comprises one or more of: conductive thread in the hood 103; and one or more proximity detectors at the hood 103.

Attention is next directed to FIG. 3 which depicts a block diagram of electrical components of the garment 101. In particular, the electrical components of the garment 101 comprise: the speaker 105, the sensor 107, the optional microphone 111, a switch 320, an optional memory 322 (as indicated by the memory 322 being drawn in dashed lines) storing an optional application 223, a communication interface 324, and a battery 399 and/or a power source which powers the electrical components. The switch 320 is electrically interconnected with the other electrical components using a bus, wires, and the like.

The switch 320 is generally configured to receive a signal from the sensor 107 indicating whether the hood 103 is deployed or undeployed and, in response, activate, or deactivate the speaker 105 (and optionally activate, or deactivate the microphone 111). The switch 320 may include, but is not limited to, one or more of an electronically activated mechanical switch, a transistor device, a controller, a processor and the like.

Furthermore, while the switch 320 is depicted as a distinct component, in other embodiments the switch 320 may be integrated with one or more of the sensor 107, speaker 105 (and/or the microphone 111, when present), and the interface 324.

Alternatively, the switch 320, the memory 322 and the interface 324 may be provided in a module that is integrated into the garment 101, for example at a location that won't interfere with the physical deployment of the hood 103 (e.g. at the neck portion 113, and the like).

When the switch 320 comprises a controller and/or a processor, the switch 320 may include one or more logic circuits configured to implement functionality for activating and deactivating the speaker 105 (and/or the microphone 111). Example logic circuits include one or more processors, one or more microprocessors, one or more ASIC (application-specific integrated circuits) and one or more FPGA (field-programmable gate arrays). In some embodiments, a controller and/or a processor of the switch 320 is not generic controller and/or a generic processor, but a device specifically configured to implement speaker and/or microphone activation/deactivation functionality.

The memory 322 of FIG. 3, when present, is a machine readable medium that stores machine readable instructions to implement one or more programs or applications. Example machine readable media include a non-volatile storage unit (e.g. Erasable Electronic Programmable Read Only Memory ("EEPROM"), Flash Memory) and/or a volatile storage unit (e.g. random access memory ("RAM")). In the embodiment of FIG. 3, programming instructions (e.g., machine readable instructions) that implement the functional teachings of the device 101 as described herein are maintained, persistently, at the memory 322 and used by a controller and/or processor of the switch 320 which makes appropriate utilization of volatile storage during the execution of such programming instructions. In particular, the memory 322 of FIG. 3 stores instructions corresponding to an application 223 that, when executed by a controller and/or processor of the switch 320, enables the switch 320 to: determine, using the sensor 107, that the hood 103 is in the undeployed state, and, in response, deactivate the speaker 105 (and/or the microphone 111); and determine, using the sensor 107, that the hood 103 is in the deployed state, and, in response, activate the speaker 105 (and/or the microphone 111).

The interface 324 is generally configured to communicate and/or wirelessly communicate, for example with the radio 109.

In some embodiments, the interface 324 comprises a wired connector to the radio 109, and the radio 109 and the interface 324 are in communication via a cable; indeed, in these implementations, the electrical components of the garment 101 may be powered by a power source at the radio 109 (e.g. via the cable) and the battery 399 may not be present at the garment 101.

In other embodiments, the interface 324 and the radio 109 communicate using, for example, one or more communication channels, the interface 324 being implemented by, for example, one or more radios and/or antennas and/or connectors and/or network adaptors, configured to communicate, for example wirelessly communicate, with network architecture that is used to communicate with the radio 109, and the like.

Indeed, the interface 324 may form a local area network and/or a personal area network, and the like, with the radio 109; for example, the interface 324 may include a one or more local area network or personal area network transceivers operating in accordance with an IEEE 802.11 standard (e.g., 802.11a, 802.11b, 802.11g), or a Bluetooth transceiver. For example, in these embodiments, when the hood 103 is deployed, and the speaker 105 and the microphone 111 are activated, audio communications of the radio 109, may be rerouted from the RSM of the radio 109 to the speaker 105 and the microphone 111; similarly, when the hood 103 is undeployed, and the speaker 105 and the microphone 111 are deactivated, audio communications of the radio 109, may be via the RSM of the radio 109.

As such, the switch 320 may be configured to transmit, to the radio 109, using the interface 324, a signal causing the radio 109 to, upon receipt of a signal from the sensor 107 indicating that the hood 103 is in the deployed state, control the radio 109 to reroute audio communications signals to the interface 324 such that the speaker 105 outputs sound that would otherwise be output at the RSM, and the microphone 111 is used to receive sound to be transmitted by the radio 109 (and that would otherwise be received at the RSM). Put another way, the switch 320 may be configured to control the radio 109 to reroute sound to the speaker 105.

Put yet another way, in these embodiments, the speaker 105 and the microphone 111 may be activated as an RSM for the radio 109 when the hood 103 is in the deployed state, and deactivated as an RSM for the radio 109 when the hood 103 is in the undeployed state.

In other embodiments, however, the interface 324 may include, but is not limited to, one or more broadband and/or narrowband transceivers, such as a Long Term Evolution (LTE) transceiver, a Third Generation (3G) (3GGP or 3GGP2) transceiver, an Association of Public Safety Communication Officials (APCO) Project 25 (P25) transceiver, a Digital Mobile Radio (DMR) transceiver, a Terrestrial Trunked Radio (TETRA) transceiver, a WiMAX transceiver operating in accordance with an IEEE 802.16 standard, and/or other similar type of wireless transceiver configurable to communicate via a wireless network for infrastructure communications. In some embodiments, the interface 324 is further configured to communicate "radio-to-radio" on some communication channels, while other communication channels are configured to use wireless network infrastructure. Example communication channels over which the interface 324 is generally configured to wirelessly communicate include, but are not limited to, one or more of wireless channels, cell-phone channels, cellular network channels, packet-based channels, analog network channels, Voice-Over-Internet ("VoIP"), push-to-talk channels and the like, and/or a combination. Indeed, the term "channel" and/or "communication channel", as used herein, includes, but is not limited to, a physical radio-frequency (RF) communication channel, a logical radio-frequency communication channel, a trunking talkgroup (interchangeably referred to herein a "talkgroup"), a trunking announcement group, a VOIP communication path, a push-to-talk channel, and the like.

In other words, the garment 101 may include a radio and/or a communication, for example at the interface 324, that may be used for remote communications, for example with a dispatch center, cell phones, first responder radios, and the like.

While not depicted, the garment 101 may further include a mechanical and/or electrical "On/Off" switch, and the like, which may be used by the wearer 102 to turn the electrical components of the garment 101 on and off (e.g. to connect and disconnect the electrical components of the garment 101 from the battery 399)

Operation of the garment 101 will be further described with reference to FIG. 4, FIG. 5, FIG. 6, and FIG. 7, each of which is similar to FIG. 3 with like elements having like numbers.

Figure 4:
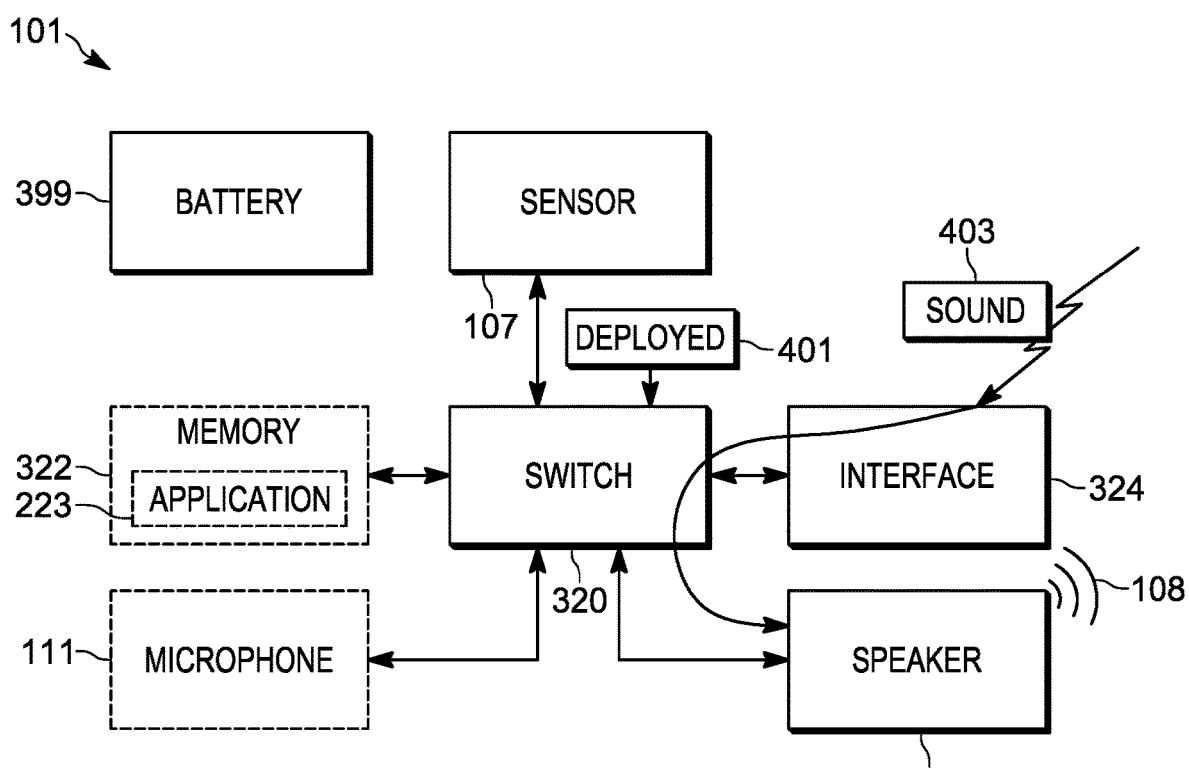
FIG. 4 depicts the speaker of the body-wearable garment being activated when the hood is in a deployed state in accordance with some embodiments.

In FIG. 4, it is assumed that the sensor 107 is sensing that the hood 103 is in the deployed state and, in response, is generating a signal 401 indicating that the hood 103 is in the deployed state. The signal 401, for example, may comprise a current indicative of a conductivity associated with the deployed state (e.g. above a threshold current), a signal from a proximity detector indicating no proximity is detected, and the like.

In response, the switch 320 activates the speaker 105 and hence a sound signal 403 received at the interface 324 is received by the speaker 105 and output by the speaker as the sound 108. For example, the switch 320 may activate a physical and/or electronic switch between the interface 324 and the speaker 105.

Figure 5:
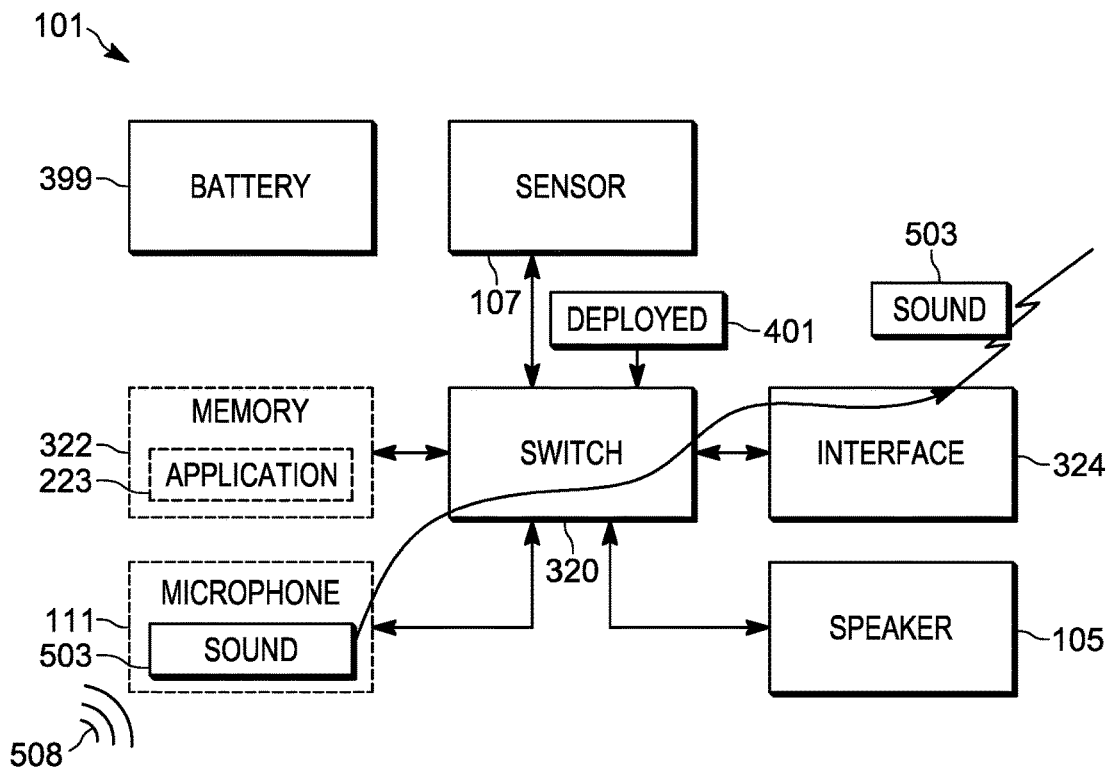
FIG. 5 depicts a microphone of the body-wearable garment being activated when the hood is in a deployed state in accordance with some embodiments.

Similarly, as depicted in FIG. 5, it is assumed that the sensor 107 is sensing that the hood 103 is in the deployed state and, in response, is generating the signal 401 indicating that the hood 103 is in the deployed state. In response, the switch 320 activates the microphone 111 and hence a sound signal 503 is conveyed from the microphone 111 to the interface 324 for transmission, for example to the radio 109. The sound signal 503 is generated upon receipt of sound 508 at the microphone 111, for example when the wearer 102 speaks into the microphone 111, and the like. For example, the switch 320 may activate a physical and/or electronic switch between the interface 324 and the microphone 111.

Figure 6:
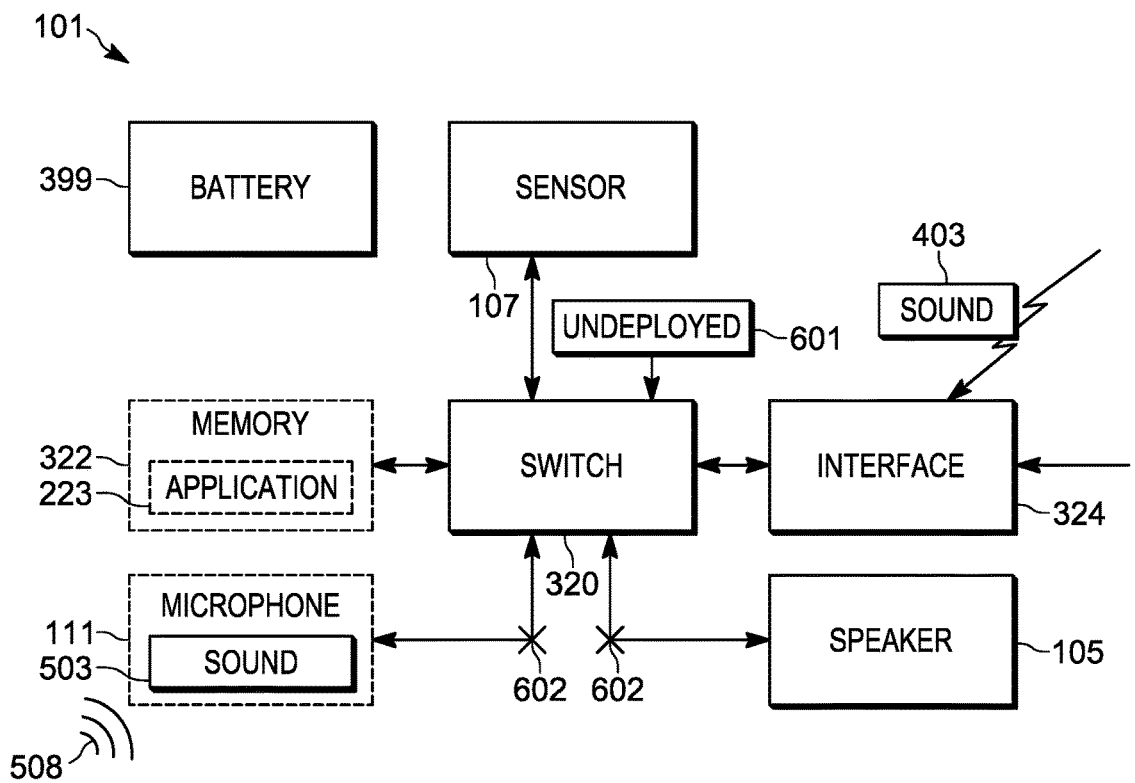
FIG. 6 depicts the speaker and the microphone of the body-wearable garment being deactivated when the hood is in an undeployed state in accordance with some embodiments.

In FIG. 6, it is assumed that the sensor 107 is sensing that the hood 103 is in the undeployed state and, in response, is generating a signal 601 indicating that the hood 103 is in the undeployed state. The signal 601, for example, may comprise a current indicative of a conductivity associated with the undeployed state (e.g. below a threshold current), a signal from a proximity detector indicating that proximity is detected, and the like.

In response, the switch 320 deactivates the speaker 105 (and the microphone 111), as schematically indicated by an "X" 602 at each of: the connection between the speaker 105 and the switch 320; and the connection between the microphone 111 and the switch 320. Hence, any sound signal 503 produced by the microphone 111 is not conveyed to the interface 324 and any sound signal 403 received at the interface 324 is not received by the speaker 105. For example, the switch 320 may deactivate a physical and/or electronic switch between the interface 324 and each of the speaker 105 the microphone 111.

Indeed, as depicted, each of the speaker 105 and/or the microphone 111 has been deactivated by placing each of the speaker 105 and/or the microphone 111 on standby in which each of the speaker 105 and/or the microphone 111 are powered, but do not have access to the interface 324 and/or are not connected to the interface 324.

Alternatively, deactivation of the speaker 105 and/or the microphone 111 may include cutting power from the battery 399 to the speaker 105 and/or the microphone 111.

Alternatively, deactivation of the speaker 105 and/or the microphone 111 may include deactivating and/or cutting power to the interface 324.

Figure 7:
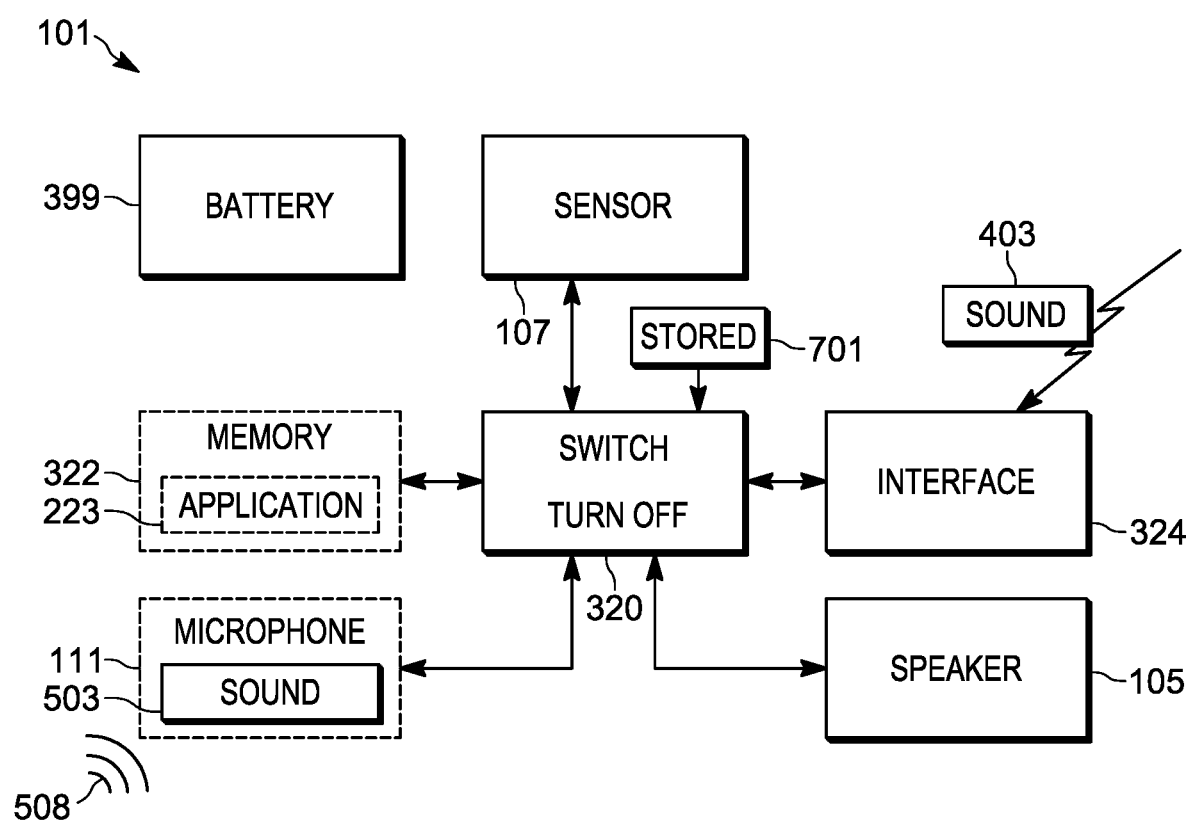
FIG. 7 depicts the speaker and the microphone of the body-wearable garment being turned off when the hood and/or the body-wearable garment are in a stored state in accordance with some embodiments.

In FIG. 7, it is assumed that the sensor 107 is sensing that the hood 103 (and/or the garment 101) is in a stored state and, in response, is generating a signal 701 indicating that the hood 103 (and/or the garment 101) is in a stored state. The signal 701, for example, may comprise a current indicative of a conductivity associated with the stored state (e.g. below a threshold current associated with the stored state), a signal from one or more proximity detectors indicating that proximity is detected at both the hood 103 and the neck portion 113, and the like.

In response, the switch 320 turns off the speaker 105 (and the microphone 111). Indeed, in some implementations, the switch 320 turns off power to all the electrical components of the garment 101 (including, but not limited to, itself (e.g. the switch 320 turns itself off when the switch 320 comprises a controller, a processor, a transistor and the like)). Hence, the switch 320 turning off power to all the electrical components of the garment 101 when the garment 101 is in a stored state may be used to ensure the electrical components of the garment 101 are off when the wearer 102 forgets to turn off the electrical components using an "On/Off" switch and the like, The stored state is schematically depicted in FIG. 8 where both the hood 103 and the neck portion 113 is folded, and the conductive thread of the sensor 107 is folded at both the hood 103 and the neck portion 113 and hence has more bends (and a higher conductivity) then in the deployed and undeployed state. Hence, it is further assumed herein that in each of the deployed state and the undeployed state the garment 101 is being worn by the wearer 102, while in the stored state, the garment 101 is not being worn by the wearer 102.

Hence, provided herein is a body-wearable garment with an integrated speaker in a hood, which may be activated quickly when the hood is deployed. A firefighter, for example, entering an IDLH environment may hence quickly don the body-wearable garment, deploy the hood and enable communications with a radio, and the like, which may save time in setting up an audio communication system, allowing the firefighter to more quickly enter the IDLH environment.

Furthermore, in embodiments where a stored state of the body-wearable garment is sensed, the electrical components of the body-wearable garment may be automatically turned off which may save battery life in the event the wearer of the garment forgets to turn off the electrical components of the garment when taking off and storing the garment.

In the embodiments of FIG. 1 to FIG. 8, it is assumed that the speaker 105 is located at a position on the interior surface of the hood 103 where the speaker 105 will be located adjacent the ear 110 of the wearer 102 when the hood 103 is in the deployed state. However, ear positions of humans vary and/or the hood 103 may not always deploy to the same position. Hence, the speaker 105 may not always be located adjacent the ear 110 of the wearer 102 when the hood 103 is in the deployed state. Similarly, the hood 103 may move while in use and the speaker 105 may correspondingly move away from the ear 110 of the wearer 102. While, in each of these situations, the wearer 102 may adjust the hood 103, in an IDLH environment the wearer 102 may not have time to do so.

Figure 9:
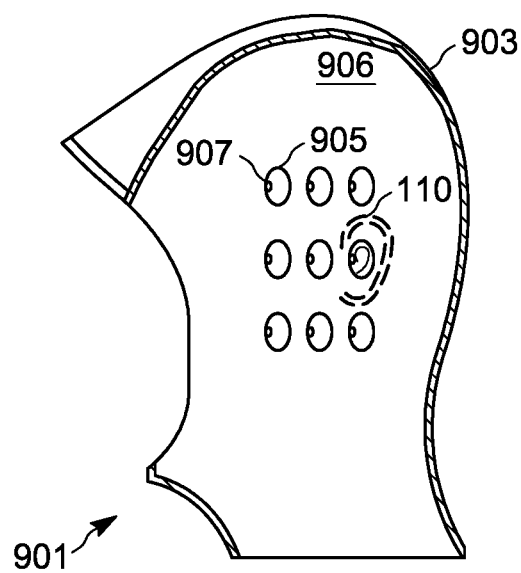
FIG. 9 is a cutaway view of a schematic diagram showing an interior surface of a body-wearable garment that includes a plurality of speakers and one or more sensors configured to sense proximity of each of the plurality of speakers to an ear of a wearer in accordance with some alternative embodiments.

Hence, attention is directed to FIG. 9 which depicts an alternative embodiment of a body-wearable garment 901, that is similar to the garment 101, and includes a hood 903 and a plurality of speakers 905 located at an interior surface 906 of the hood 903 and one or more second sensors 907 configured to sense proximity of each of the plurality of speakers 905 to the ear 110 (depicted in outline) of a wearer of the garment 901. While not depicted, it is assumed that the garment 901 otherwise has a similar structure and electrical components as the garment 101 depicted in FIG. 1, FIG. 2 and FIG. 3. For example, while not depicted the garment 901 may include a sensor similar to the sensor 107. However, in some implementations, the garment 901 does not include a sensor similar to the sensor 107, and the speakers 905 are activated as described below independent of whether the hood 903 is deployed; for example, the speakers 905 may be activated as described below when the electrical components of the garment 901 are turned on via an "On/Off" switch, and the like.

As depicted, there are nine speakers 905 arranged in a grid pattern, with a respective sensor 907 associated with each speaker 905. As depicted, each sensor 907 is integrated into a respective speaker 905, however, each sensor 907 may alternatively be located adjacent a respective speaker 905.

Each sensor 907 is generally configured to detect proximity of the ear 110. For example, each sensor 907 may comprise a proximity detector, and/or a temperature sensor and/or a thermal sensor.

When a sensor 907 comprises a proximity sensor, detection of proximity of the ear 110 may be based on the proximity sensors 907 measuring proximity of adjacent parts of the head of the wearer 102. A proximity sensor 907 adjacent the entrance of the ear canal of the ear 110 may produce a lower proximity signal than the other proximity sensors 907, as the ear canal will be further away from the proximity sensor 907 adjacent the entrance of the ear canal than other respective parts of the wearer's head are to the other proximity sensors 907. Hence, the speaker 905 associated with the proximity sensor 907 producing the lowest proximity signal is selected as the speaker 905 to activate, for example when the hood 903 is deployed.

Similarly, when a sensor 907 comprises a temperature sensor, detection of proximity of the ear 110 may be based on the temperature sensors 907 measuring temperature of adjacent parts of the head of the wearer 102. A temperature sensor 907 adjacent the entrance of the ear canal of the ear 110 may measure a lower temperature than the other temperature sensors 907, as the ear canal will be further away from the temperature sensor 907 adjacent the entrance of the ear canal than other respective parts of the wearer's head will be to the other temperature sensors 907. Hence, the speaker 905 associated with the temperature sensor 907 producing the lowest temperature is selected as the speaker 905 to activate, for example when the hood 903 is deployed.

As depicted, the ear 110 is adjacent the right-most speaker 905 in the second row of the grid of the speakers 905, and hence this speaker 905 is selected for activation, for example when the hood 903 is deployed.

Indeed, a switch of the garment 901 (e.g. similar to the switch 320 and assuming the switch of the garment 901 comprises a controller and/or a processor and the like) may be adapted for selecting a speaker 905 for activation, from a plurality of speakers 905, the speaker 905 being activated in response to both: receiving a signal from the sensor (e.g. similar to the sensor 107) indicating that the hood 903 is in the deployed state; and receiving another signal from one or more second sensors 907 indicating that the speaker 905 is a closest speaker, of the plurality of speakers 905, to the ear 110 of the wearer 102.

Furthermore, the switch of the garment 901 may monitor the sensors 907 while the hood 903 is in the deployed state; one of the speakers 905 may initially be activated as a closest speaker. However, when another speaker 905 becomes the closest speaker, as determined using the sensors 907, the closest speaker is activated, and the previously activated speaker 905 is deactivated. Hence, as the hood 903 shifts while being worn, different speakers 905 are activated based on ear proximity to ensure that the wearer 102 of the hood 903 may hear the audio, for example from the radio 109.

While the embodiment of FIG. 9 is described with respect to proximity sensors and temperature sensors, other types of sensors may be used to detect proximity of the ear 110 to a plurality of speakers. For example, attention is directed to FIG. 10 and FIG. 11, which depict an alternative embodiment of a body-wearable garment 1001, that is similar to the garment 901, and includes: a hood 1003 and a plurality of speakers 1005 located at an interior surface 1006 of the hood 1003, and a second sensor 1007 configured to sense proximity of each of the plurality of speakers 1005 to the ear 110 (depicted in outline) of a wearer 102 (also depicted in outline) of the garment 1001. While not depicted, it is assumed that the garment 1001 otherwise has a similar structure and electrical components as the garment 101 depicted in FIG. 1 and FIG. 3, and that the speakers 1005 are similar to the speakers 905. For example, while not depicted the garment 1001 may include a sensor similar to the sensor 107. However, in some implementations, the garment 1001 does not include a sensor similar to the sensor 107, and the speakers 1005 are activated as described below independent of whether the hood 1003 is deployed; for example, the speakers 1005 may be activated as described below when the electrical components of the garment 1001 are turned on via an "On/Off" switch, and the like.

As depicted, the sensor 1007 comprises an electroencephalogram (EEG) sensor, located on the interior surface 1006 of the hood 1003 at a position where the sensor 1007 may contact the head of the wearer 102 in order to detect an EEG signal from the wearer 102. Indeed, the sensor 1007 may include an adhesive surface for promoting contact with the head of the wearer 102. While in FIG. 10, and FIG. 11, the sensor 1007 is located at the base of the head of the wearer 102, the sensor 1007 may be located in any position that may detect EEG signals from the wearer 102. For example, the sensor 1007 may be integrated into a headband worn around the head of the wearer 102 in conjunction with the hood 1003, and/or such a headband may be integrated with the hood 1003.

Figure 10:
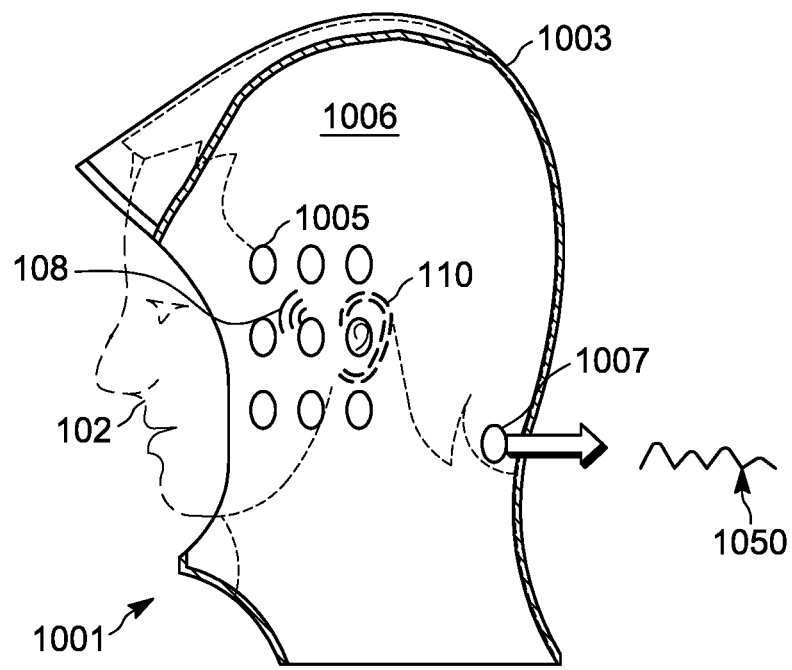
FIG. 10 is a cutaway view of a schematic diagram showing an interior surface of a body-wearable garment that includes a plurality of speakers and an electroencephalogram sensor producing an electroencephalogram signal in accordance with some alternative embodiments.
Figure 11:
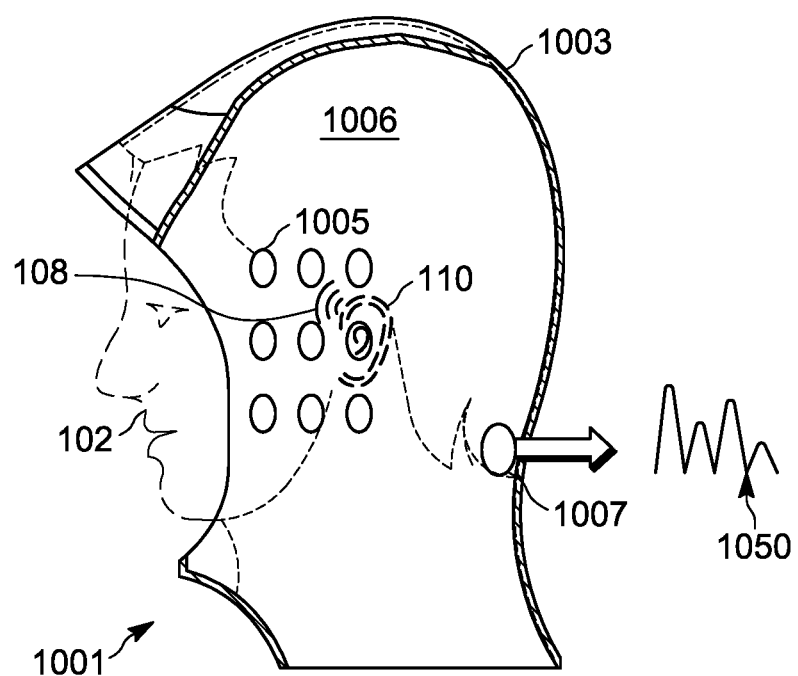
FIG. 11 is a cutaway view of a schematic diagram showing an interior surface of the body-wearable garment of FIG. 10, the electroencephalogram sensor producing a higher electroencephalogram signal in accordance with some alternative embodiments.

In each of FIG. 10 and FIG. 11, the EEG sensor 1007 is producing a respective EEG signal 1050, 1150. However, as depicted in FIG. 10, an activated speaker 1005 emitting sound 108 is not the closest speaker to the ear 110, while in FIG. 11, another activated speaker 1005 emitting sound 108 is the closest speaker to the ear 110. Hence, the EEG signal 1050 in FIG. 10 is smaller than the EEG signal 1150 in FIG. 11. Hence, the speaker 1005 emitting sound 108 in FIG. 11 is selected to output the sound 108.

In other words, a switch of the garment 1001 (e.g. similar to the switch 320 and assuming the switch of the garment 1001 comprises a controller and/or a processor and the like) may be adapted for selecting a speaker 1005 for activation by activating two or more of the speaker 1005 in a sequence and receiving an EEG signal from the EEG sensor 1007. The speaker 1005 that results in the highest EEG signal will be activated, for example in response to the hood 1003 being in the deployed state. Furthermore, the speaker selection process may be repeated periodically.

Figure 12:
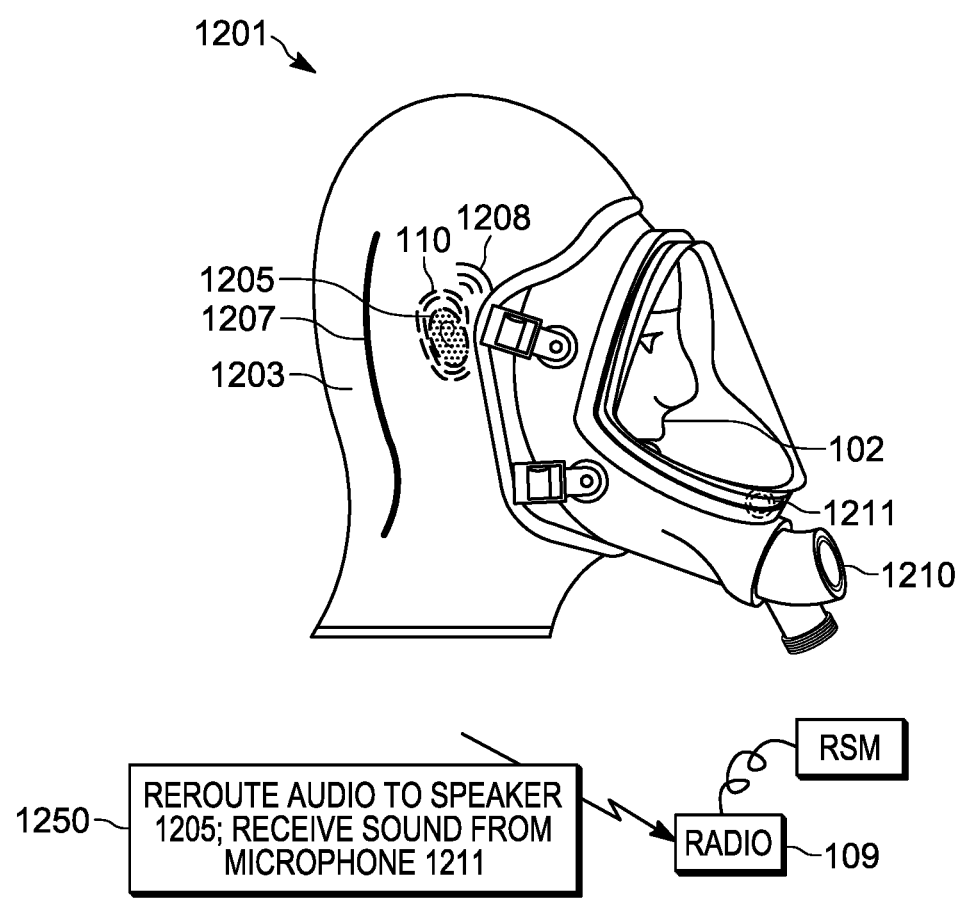
FIG. 12 is a schematic diagram of a body-wearable garment that includes a speaker in a hood, and an optional in a mask, each which are activated when the hood is in a deployed state and deactivated when the hood in undeployed state, in accordance with some embodiments.

Attention is next directed to FIG. 12 which depicts an alternative embodiment of a body-wearable garment 1201, that is similar to the garment 101, and includes a hood 1203 (depicted in a deployed state) and a speaker 1205 located at an interior surface of the hood 1203, as well as a sensor 1207 similar to the sensor 107. While not depicted, it is assumed that the garment 1201 otherwise has a similar structure and electrical components as the garment 101 depicted in FIG. 1, FIG. 2 and FIG. 3.

However, in contrast to the garment 101, one or more of the garment 1201 and the hood 1203 is depicted in use with a mask 1210, including, but not limited to, a self-contained breathing apparatus (SCBA) mask, and the like. Furthermore, the garment 101 does not include a microphone, however the mask 1210 includes a microphone 1211 which may be used in place of a microphone of the RSM of the radio 109. While not depicted, it is assumed that the mask 1210 includes electrical components that enables the microphone 1211 to communicate (in wired and/or wireless manner) with the radio 109, as well a battery, and the like to power the electrical components (and/or a connection with a battery of the garment 1201 and/or the radio 109).

For example, when the sensor 1207 senses that the hood 1203 is in a deployed state, as depicted, a switch of the garment 1201 (e.g. similar to the switch 320, assuming the switch of the garment 1201 includes a controller and/or a processor and the like) transmits a signal 1250 to the radio 109 (e.g. using a communication interface similar to the interface 324), the signal 1250 comprising a command that causes the radio 109 to reroute audio signal received at the radio 109 (e.g. via a respective wireless communication interface, not depicted) to the speaker 1205 (output as sound 1208 into the ear 110 of the wearer 102), and to receive sound from the microphone 1211. Thereafter, the radio 109 reroutes audio signals to the speaker 1205 and receives sound signals for transmission from the microphone 1211.

While present embodiments have been described with respect to activating a speaker in a hood in response to receiving a signal from a sensor indicating that the hood is in a deployed state, such signals from such sensors may be used to activate other types of electrical devices. For example, in addition to a speaker and/or a microphone, a light at a hood and the like could be activated and deactivated based on the hood being in a deployed state or undeployed state. Furthermore, the electrical devices could be integrated into other types of body-wearable garments that don't include a hood, but include another type of portion that may be deployed (and/or unfolded) and undeployed (and/or folded), including, but not limited to, ear flaps on hat. For example, the hat could include a head warming device (e.g. a heater) that is activated (e.g. turned on) when the ear flaps are unfolded (e.g. deployed) over the ears of a wearer, and deactivated with the ear flaps are folded (e.g. undeployed).

Hence, generally described herein is a body-wearable garment that comprises a deployable portion; and an electrical device, the electrical device being activated in response to receiving a signal from a sensor indicating that the deployable portion is in a deployed state, the electrical device being deactivated in response to receiving a signal from the sensor indicating that the deployable portion is in an undeployed state.

In the foregoing specification, specific embodiments have been described. However, one of ordinary skill in the art appreciates that various modifications and changes may be made without departing from the scope of the invention as set forth in the claims below. Accordingly, the specification and figures are to be regarded in an illustrative rather than a restrictive sense, and all such modifications are intended to be included within the scope of present teachings.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

In this document, language of "at least one of X, Y, and Z" and "one or more of X, Y and Z" may be construed as X only, Y only, Z only, or any combination of two or more items X, Y, and Z (e.g., XYZ, XY, YZ, ZZ, and the like).

Similar logic may be applied for two or more items in any occurrence of "at least one . . . " and "one or more . . . " language.

Moreover in this document, relational terms such as first and second, top and bottom, and the like may be used solely to distinguish one entity or action from another entity or action without necessarily requiring or implying any actual such relationship or order between such entities or actions. The terms "comprises," "comprising," "has", "having", "includes", "including," "contains", "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a", "has . . . a", "includes . . . a", "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially", "essentially", "approximately", "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The term "coupled" as used herein is defined as connected, although not necessarily directly and not necessarily mechanically. A device or structure that is "configured" in a certain way is configured in at least that way, but may also be configured in ways that are not listed.

It will be appreciated that some embodiments may be comprised of one or more generic or specialized processors (or "processing devices") such as microprocessors, digital signal processors, customized processors and field programmable gate arrays (FPGAs) and unique stored program instructions (including both software and firmware) that control the one or more processors to implement, in conjunction with certain non-processor circuits, some, most, or all of the functions of the method and/or apparatus described herein. Alternatively, some or all functions could be implemented by a state machine that has no stored program instructions, or in one or more application specific integrated circuits (ASICs), in which each function or some combinations of certain of the functions are implemented as custom logic. Of course, a combination of the two approaches could be used.

Moreover, an embodiment may be implemented as a computer-readable storage medium having computer readable code stored thereon for programming a computer (e.g., comprising a processor) to perform a method as described and claimed herein. Examples of such computer-readable storage mediums include, but are not limited to, a hard disk, a CD-ROM, an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory. Further, it is expected that one of ordinary skill, notwithstanding possibly significant effort and many design choices motivated by, for example, available time, current technology, and economic considerations, when guided by the concepts and principles disclosed herein will be readily capable of generating such software instructions and programs and ICs with minimal experimentation.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it may be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

I claim:

1. A body-wearable garment, comprising:
   a hood;
   a speaker integrated within the hood, the speaker being activated in response to receiving a signal from a sensor indicating that the hood is in a deployed state;
   a plurality of speakers, including the speaker; and
   one or more second sensors configured to sense proximity of each of the plurality of speakers to an ear of a wearer of the hood, the speaker being activated in response to both: receiving the signal from the sensor indicating that the hood is in the deployed state; and receiving another signal from the one or more second sensors indicating that the speaker is a closest speaker, of the plurality of speakers, to the ear of the wearer.

2. The body-wearable garment of claim 1, wherein the sensor is configured to sense whether the hood is in an undeployed state or the deployed state.

3. The body-wearable garment of claim 1, wherein the sensor is configured to: sense the hood being in an undeployed state when the hood is folded; and sense the hood being in the deployed state when the hood is unfolded.

4. The body-wearable garment of claim 1, wherein the speaker is one or more of deactivated and placed on standby in response to receiving another signal from the sensor indicating that the hood is in an undeployed state.

5. The body-wearable garment of claim 1, wherein the sensor comprises one or more of: conductive thread in the hood; and one or more proximity detectors at the hood.

6. The body-wearable garment of claim 1, wherein the speaker is turned off in response to receiving a signal from the sensor indicating that the hood is in a stored state.

7. The body-wearable garment of claim 1, further comprising a microphone, the microphone being activated in response to receiving the signal from the sensor indicating that the hood is in the deployed state.

8. The body-wearable garment of claim 1, wherein the one or more second sensors comprises one or more of: a proximity sensor; a temperature sensor; a thermal sensor; and an electroencephalogram sensor.

9. The body-wearable garment of claim 1, wherein the plurality of speakers is arranged in a grid pattern at an interior of the hood, and a respective sensor, of the one or more second sensors, is one or more of: integrated with a respective speaker, of the plurality of speakers; and located adjacent the respective speaker.

10. The body-wearable garment of claim 1, wherein the one or more second sensors comprises an electroencephalogram sensor integrated with one or more of the hood and a headband.

11. The body-wearable garment of claim 1, further comprising a switch configured to:
   determine, using the sensor, that the hood is in an undeployed state, and, in response, deactivate the speaker; and
   determine, using the sensor, that the hood is in the deployed state, and, in response, activate the speaker.

12. The body-wearable garment of claim 11, wherein the switch is further configured to:
   determine, using the sensor, that the hood is in a stored state, and, in response, turn off the speaker.

13. The body-wearable garment of claim 11, wherein the switch is further configured to:
   communicate with a radio; and
   when the hood is in the deployed state, control the radio to reroute audio signals to the speaker.

14. The body-wearable garment of claim 11, further comprising a microphone, and wherein the switch is further configured to:
   communicate with a radio; and
   when the hood is in the deployed state, control the radio to receive sound signals for transmission from the microphone.

15. The body-wearable garment of claim 11, wherein the switch is further configured to:
   communicate with a radio;
   communicate with a microphone in a mask; and
   when the hood is in the deployed state, control the radio to receive sound signals for transmission from the microphone.

16. The body-wearable garment of claim 11, further comprising a communication interface, wherein the switch is further configured to, when the hood is in the deployed state, reroute audio signals from a radio to the speaker via the communication interface.

17. The body-wearable garment of claim 1, wherein the speaker is flexible.

18. The body-wearable garment of claim 1, wherein the hood comprises a fire-retardant material.

19. The body-wearable garment of claim 1, wherein the hood is adapted for use with one or more of a mask and a self-contained breathing apparatus mask.

* * * * *